United States Patent [19]

Beck et al.

[11] Patent Number: 4,748,243
[45] Date of Patent: May 31, 1988

[54] PREPARATION OF 2-CHLORO-5-CHLOROMETHYLTHIAZOLE

[75] Inventors: Gunther Beck; Helmut Heitzer, both of Leverkusen, Fed. Rep. of Germany

[73] Assignee: Bayer Aktiengesellschaft, Leverkusen, Fed. Rep. of Germany

[21] Appl. No.: 91,577

[22] Filed: Aug. 31, 1987

[30] Foreign Application Priority Data

Sep. 17, 1986 [DE] Fed. Rep. of Germany ....... 3631538

[51] Int. Cl.$^4$ .......................................... C07D 277/32
[52] U.S. Cl. ...................... 548/202; 548/205
[58] Field of Search .......................... 548/202

[56] References Cited

U.S. PATENT DOCUMENTS 4,013,674  3/1977  Beck .................... 548/202

FOREIGN PATENT DOCUMENTS 192060  8/1986  European Pat. Off. .
5972    1/1979  Japan .

OTHER PUBLICATIONS

Metzger, Thiazole and its Derivatives, pp. 273–274 (1979).
E. Kühle, B. Anders and G. Zumach; Isocyanid-dihalogenidynthesen–Syntheses, Chemie 79, 663 (1967).
J. Amer. Chem. Soc. 56, pp. 470–471, J. Amer. Chem. Soc. 104, pp. 4461–4465, J. Amer. Chem. Soc. Perkin I, 1982, pp. 159–164.

Primary Examiner—Robert Gerstl
Attorney, Agent, or Firm—Sprung Horn Kramer & Woods

[57] ABSTRACT

A process for the preparation of 2-chloro-5-chloromethyl-thiazole of the formula:

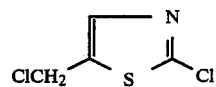

comprising reacting allyl isothiocyanate of the formula

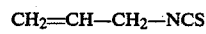

with about 2 to 20 times its molar amount of chlorine at a temperature from above 0° to 150° C.

7 Claims, No Drawings

PREPARATION OF 2-CHLORO-5-CHLOROMETHYLTHIAZOLE

The present invention relates to a new process for the preparation of the known compound 2-chloro-5-chloromethylthiazole.

The compound 2-chloro-5-chloromethylthiazole was disclosed in the published European patent application No. 192,060. In this, see, for example, page 81, line 13.

On the preparation of 4-halogenomethylthiazoles, the following is stated on page 93, lines 1 to 24:

"4-Halogenomethylthiazoles can be synthesized directly, for example by reacting dihalogenoacetones with thioacetylamides, such as thioacetamide (J. Amer. Chem. Soc. 56, pp. 470–471 and ibid. 73, p. 2936).

5-Halogenomethylthiazoles can be obtained by reacting a thiacylamide with α-chloro-α-formylethyl acetate, reducing the resultant 5-ethoxycarbonylthiazole in a conventional fashion using lithium aluminum hydride, and halogenating the resultant 5-hydroxymethylthiazole. 5-Chloromethyl-2-methylthiazole, which is described in Zh. Obshch. Khim. 32, pp. 570–575, and in J. Amer. Chem. Soc. 104, pp. 4461–4465, is a good example.

The reaction of thiourea in place of the thioacylamide is capable of giving 2-amino-4-chloromethyl- or 2-amino-5-chloromethylthiazole, and a halogen atom, etc., can furthermore be introduced through diazotization. This halogen is active and can be converted into a 2-alkoxy group with the aid of a sodium alkoxide (JP-OS (Japanese published specification No.) 5972/1979 and J. Chem. Soc. Perkin I, 1982, pp. 159–164)."

The abovementioned processes are time-consuming and usually associated with only a very poor yield.

It has been found that 2-chloro-5-chloromethylthiazole I

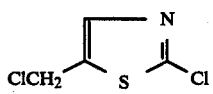

(I)

is obtained in a simple fashion by allowing 2 to 20 moles of chlorine to act on each mole of allyl isothiocyanate (=allyl mustard oil) of the formula $$CH_2=CH-CH_2-NCS \quad (II)$$

at temperatures from 0° C. to 150° C., if appropriate in a diluent which is inert under the reaction conditions.

It can be described as extremely surprising that 2-chloro-5-chloromethylthiazole can be prepared according to the reaction according to the invention since it was known that aliphatic and cycloaliphatic mustard oils are converted by chlorination into isocyanide dichlorides in 70 to 95% yield (cf. E. Kühle, B. Anders and G. Zumach: Isocyaniddihalogenid-Synthesen [Isocyanide dihalide syntheses], Angewandte Chemie 79, 663 (1967)).

The equation for the reaction according to the invention can be illustrated as follows:

(II)

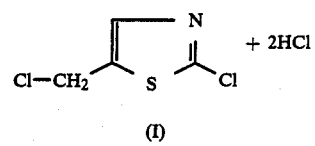

(I)

Chlorinating agents are taken to mean chlorine and compounds which dechlorinate under the reaction conditions, such as, for example, sulphuryl chloride, which dechlorinates to produce elemental chlorine according to the overall equation $$SO_2Cl_2 \rightarrow SO_2 + Cl_2$$

In the following, the term chlorine is taken to mean both elemental chlorine employed from the beginning and chlorine liberated from compounds which dechlorinate under the reaction conditions.

As can be seen from the equation for the reaction of allyl isothiocyanate (II) with $Cl_2$ to produce 2-chloro-5-chloromethylthiazole (I), at least 2 moles of chlorine must be employed per mole of allyl mustard oil in order to achieve complete reaction. In general, large excesses of chlorine gas, which may be up to 20 moles of $Cl_2$ per mole of (II), are generally preferred. The reaction is preferably carried out using 5 to 15 moles of $Cl_2$ per mole of (II).

The chlorination reaction is expediently carried out in a diluent which is inert under the reaction conditions. Such diluents which may be mentioned are: methylene chloride, chloroform, tetrachloromethane, tetrachloroethane, pentachloroethane, trichloroethylene and tetrachloroethylene. Chloroform is preferred.

When sulphuryl chloride is used as chlorinating agent, the reaction can also be carried out in the absence of an inert diluent.

The chlorination reaction can be carried out in the temperature range from 0° C. to 150° C.; the temperature range from 30° C. to 100° C. is preferred.

The chlorination reaction can be carried out by mixing allyl isothiocyanate (II) with an equal to tenfold volume of the diluent and reacting with chlorine in the temperature range specified. However, a procedure is preferably followed in which allyl mustard oil (II) (if appropriate as a mixture with the diluent), in a chlorine-saturated diluent under constant further addition of excess chlorine (detectable through the green color of the waste gas), is metered in to an extent such that the excess of chlorine is ensured at any point in time during the chlorination reaction. It is particularly preferred to carry out this described type of chlorination at the respective boiling point (under reflux) of the diluent, that is to say, for example, at about 60° C. in the case of chloroform. In order to achieve the most complete reaction possible, it is expedient, in addition, to continue the chlorination for a further 0.1 to 2 hours at the same temperature after completing the metering in (for example dropwise addition or pumped addition) of allyl isothiocyanate.

2-Chloro-5-chloromethylthiazole (I) is the major reaction product under the abovementioned, preferred reaction conditions. In addition, it is noted as particularly advantageous that 2-chloro-5-chloromethylthiazole (I) represents the lowest-boiling reaction product when the reaction is complete and can thereby easily be obtained in the pure state by fractional distillation, for example on a column, expediently in vacuo (preferably an oil pump or water-jet pump). In order to prevent undesired thermal decomposition reactions, it is particularly advantageous for the separation of 2-chloro-5-chloromethylthiazole (I) from higher-boiling side reaction products to be carried out by means of a thin-film evaporator which is suitable for fractionation. Of course—in particular when working on a gram scale—chromato—graphic separation methods can be employed for isolating pure 2-chloro-5-chloromethylthiazole (I).

Another way of isolating pure 2-chloro-5-chloromethylthiazole (I) comprises initially allowing half to twice, preferably an equal amount by weight, relative to allyl isothiocyanate employed, of formic acid to act on the crude mixture, when the chlorination reaction is complete, at room temperature until gas evolution is complete. In this procedure, the major part of the higher-boiling byproducts is converted into sparingly soluble solids and/or oils which are removed by filtration and/or decanting. The excess formic acid is expediently removed before distilling the 2-chloro-5-chloromethylthiazole by extracting the organic phase by shaking with water or by neutralizing using the aqueous solution of an alkali metal hydroxide or alkaline-earth metal hydroxide, preferably using sodium hydroxide solution.

As described in the published European patent application No. 192,060, 2-chloro-5-chloromethylthiazole (I) is an important intermediate for the preparation of compounds which have a very great insecticidal activity, for example those having the formulae (III), (IV) and (V):

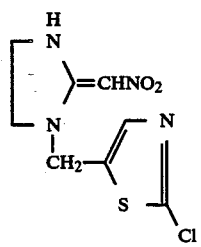
(III)

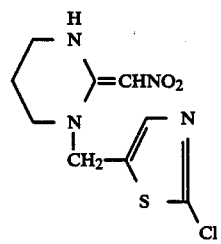
(IV)

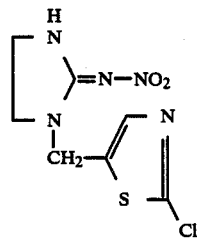
(V)

The following reactions being carried out, for example, in order to obtain the abovementioned active compounds (III), (IV) and (V):

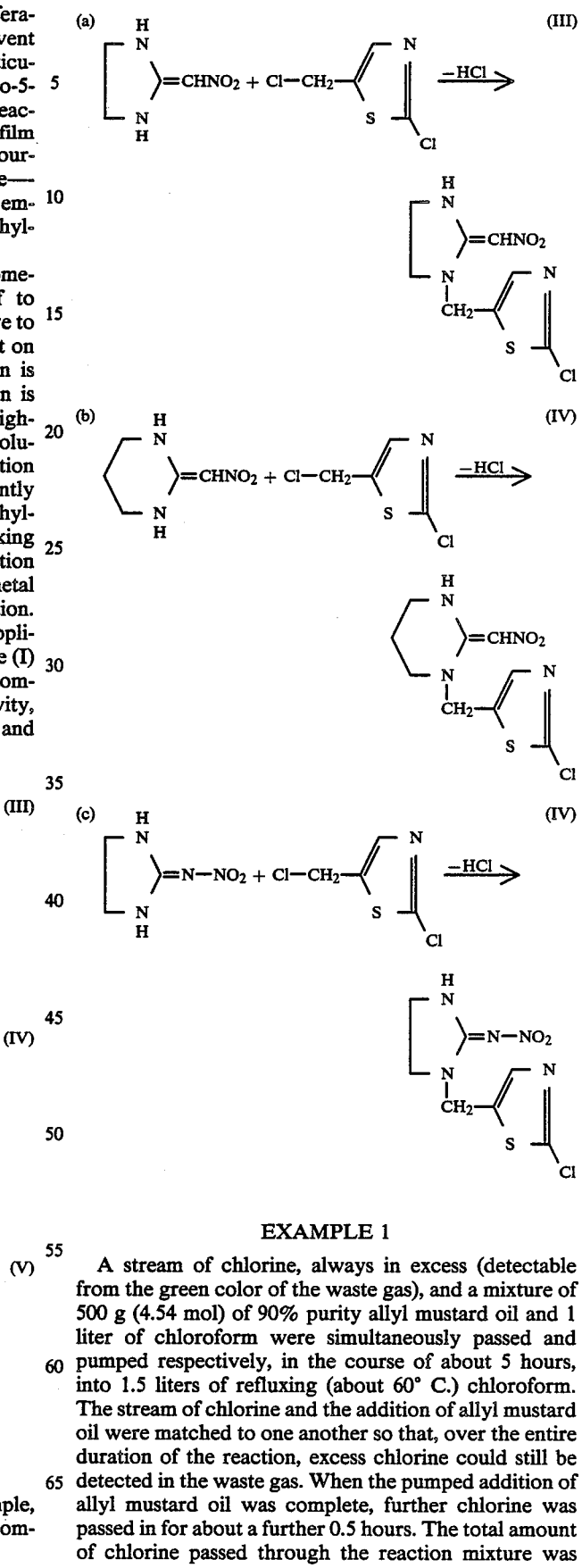

EXAMPLE 1

A stream of chlorine, always in excess (detectable from the green color of the waste gas), and a mixture of 500 g (4.54 mol) of 90% purity allyl mustard oil and 1 liter of chloroform were simultaneously passed and pumped respectively, in the course of about 5 hours, into 1.5 liters of refluxing (about 60° C.) chloroform. The stream of chlorine and the addition of allyl mustard oil were matched to one another so that, over the entire duration of the reaction, excess chlorine could still be detected in the waste gas. When the pumped addition of allyl mustard oil was complete, further chlorine was passed in for about a further 0.5 hours. The total amount of chlorine passed through the reaction mixture was 3,050 g. After the supply of chlorine was terminated, dry nitrogen was passed into the still refluxing reaction mixture in order to expel chlorine and hydrogen chloride, the mixture was then cooled to room temperature, and the solvent was subsequently removed in a rotary evaporator in a water-pump vacuum to a bath temperature of about 40° C. 1,222 g of a clear, orange-yellow oil were thus obtained. Gas-chromatographic and mass-spectroscopic analysis showed that a reaction mixture was present in which the lowest-boiling reaction product, with a percentage proportion of 41.1%, represented the major product. It proved to be 2-chloro-5-chloromethylthiazole, which had been produced in a yield, determined by gas chromatography, of 65.8% of theory. Careful distillation over a simple distillation bridge on an oil pump (about 0.1 mbar at the beginning and end, with a pressure decrease of up to about 1.5–2 mbar) in the interim, at a heating-bath temperature of 100°–140° C. produced 805.5 g of a distillate in which, according to gas-chromatographic analysis, the lowest-boiling compound, with a percentage proportion of 47.8%, represented the major product 2-chloro-5-chloromethylthiazole (corresponding to 50.4% of theory). Fractional distillation on a column of length 150 cm produced, at 50° C./1 mbar, pure 2-chloro-5-chloromethylthiazole. $^1$H-NMR (CDCl$_3$; $\delta$ TMS $=0$)

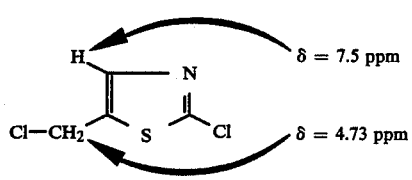

The colorless pure compound solidifies at room temperature to form long needles. Melting point: 31° C.

EXAMPLE 2

An analogous procedure to Example 1 was carried out, with the difference that a total of 3,940 g of chlorine gas were passed through the reaction mixture. Gas-chromatographic (GC) analysis of the crude product (1,250 g), freed of solvent, produced a percentage proportion of 41.3% of 2-chloro-5-chloromethylthiazole, corresponding to a GC yield of 67.6% of theory.

EXAMPLE 3

Chlorine, always in excess, and a mixture of 500 g (4.54 mols) of 90% purity allyl mustard oil and 0.5 liter of chloroform were simultaneously passed and pumped respectively, over a period of 4.25 hours, into 2.5 liters of refluxing chloroform. Further excess chlorine was subsequently passed in for about a further 0.5 hours. The total amount of chlorine passed through the reaction mixture was 1,990 g. After expelling chlorine and hydrogen chloride by passing in dry nitrogen, 500 ml of pure formic acid were added dropwise, at room temperature with stirring and cooling, at a rate such that the temperature of the reaction mixture remained between 15° and 25° C. Stirring was continued in this temperature range until gas evolution could no longer be observed. 500 ml of water were subsequently added dropwise at about 20° C., with stirring and cooling, the solid which had precipitated was filtered off or the oil which had deposited and which was insoluble in the chloroform phase was decanted off, and the clear chloroform phase was separated off and washed five times in a separating funnel with 3 liters of water in each case until a pH of about 4 had been reached. The chloroform phase was subsequently dried using sodium sulphate and the chloroform was stripped off on a rotary evaporator. The residue was roughly fractionated via a simple distillation bridge in a water-pump vacuum. 331 g of a distillate which, according to gas-chromatographic analysis, was 79.5% (corresponding to 34.5% of theory) 2-chloro-5-chloromethylthiazole were obtained at a heating-bath temperature of 120° to 150° C. and a pressure between 18 and 28 mbar. Fine fractionation on a column produced pure 2-chloro-5-chloromethylthiazole, identical to the product in Example 1.

EXAMPLE 4

An analogous procedure to Example 1 was initially carried out, with the difference that, including the subsequent chlorination, 3,450 g of chlorine were passed through the reaction mixture within 6.25 hours. The mixture was subsequently stirred at about 20° C. with 500 ml of pure formic acid until the gas evolution had ceased. 22.5% strength aqueous sodium hydroxide solution was then added dropwise, with ice cooling and with vigorous stirring at 0°–10°C., until pH 7 was reached (consumption about 2,550 ml), the greasy precipitate which had deposited was filtered off, the filtrate was separated in a separating funnel into a chloroform and a water phase, the water phase was again extracted twice by shaking with chloroform, and the combined chloroform phases were concentrated in a rotary evaporator. The residue was roughly fractionated via a simple distillation bridge in a water-pump vacuum. An initial fraction of 92 g, which, according to a gas chromatogram (GC), contained 12.6% (corresponding to a yield of 1.5% of theory) of 2-chloro-5-chloromethylthiazole, was obtained at a heating-bath temperature of 90°–120° C. and a pressure of about 20 mbar. The main fraction (220 g), which distilled at about 112° C. with 10 mbar, was, according to gas-chromatographic analysis, 84.1 per cent 2-chloro-5-chloromethylthiazole (corresponding to 24.2% of theory). Fine fractionation on a column produced pure 2-chloro-5-chloromethylthiazole, identical to the product in Example 1.

EXAMPLE 5

A stream of chlorine, always in excess, and a mixture of 125 g (1.136 mols) of 90% purity allyl mustard oil and 250 ml of methylene chloride were simultaneously passed and pumped respectively, in the course of 1.25 hours, into 375 ml of refluxing (about 40° C.) methylene chloride. When the pumped addition of allyl mustard oil was complete, further chlorine was passed in for a further 0.5 hours. The total amount of chlorine passed through the reaction mixture was 1,020 g. When the supply of chlorine was terminated, dry nitrogen was passed through the mixture, as described in Example 1, and the solvent was subsequently removed. 324 g of a clear, yellow oil which, according to GC analysis, was 31.2% 2-chloro-5-chloromethylthiazole were obtained. This works out at a yield, determined by gas chromatography, of 53.0% of theory.

EXAMPLE 6

In the course of about two hours, 500 g (4.5 mols) of 90% purity allyl isothiocyanate were pumped into 3,375 g (25 mols) of refluxing (about 69° C.) sulfuryl chloride.

The mixture was subsequently refluxed for a further hour. After removing the excess sulfuryl chloride by distillation in a water-pump vacuum in a rotary evaporator and further heating at 40° C. to 0.1 mbar (oil pump), 1,276.4 g of a yellow oil which, according to gas-chromatographic analysis, was 33.6% 2-chloro-5-chloromethylthiazole remained. This works out to a yield, determined by gas chromatography, of 56.2% of theory.

EXAMPLE 7

In the course of about 5.5 hours, 100 g (0.9 mol) of 90% purity allyl isothiocyanate were pumped into 675 g (5 mols) of refluxing sulphuryl chloride. The mixture was subsequently refluxed for a further hour. The crude product (262.6 g) obtained after removing the excess sulphuryl chloride by distillation in a water-pump vacuum in a rotary evaporator to 40° C. was subsequently distilled in a thin-film evaporator at 100°–110° C./0.1 mbar. The pale yellow distillate weighed 189.4 g and contained, according to gas-chromatographic analysis, 42.4% of 2-chloro-5-chloromethylthiazole. This works out to a yield, determined gas chromatographically, of distilled product of 52.6% of theory.

It will be understood that the specification and examples are illustrative but not limitative of the present invention and that other embodiments within the spirit and scope of the invention will suggest themselves to those skilled in the art.

We claim:
1. A process for the preparation of 2-chloro-5-chloromethyl-thiazole of the formula

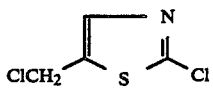

comprising reacting allyl isothiocyanate of the formula

with about 2 to 20 times its molar amount of chlorine at a temperature from above 0° to 150° C.

2. A process according to claim 1, wherein the chlorine is supplied in the form of elemental chlorine.

3. A process according to claim 1, wherein the chlorine is supplied in the form of a chlorinating agent which dechlorinates to form elemental chlorine.

4. A process according to claim 1, wherein the chlorine is employed in about 5 to 15 times the molar amount and the temperature is from about 30 to 100° C.

5. A process according to claim 1, wherein the reaction is effected in the presence of an inert diluent 6. A process according to claim 5, wherein the inert diluent is dichloromethane or trichloromethane.

7. A process according to claim 5, wherein the allyl isothiocyanate is metered into a boiling diluent containing chlorine in excess.